United States Patent [19]
Levin

[11] Patent Number: 5,813,410
[45] Date of Patent: Sep. 29, 1998

[54] INTERNAL BODY PUMP AND SYSTEMS EMPLOYING SAME

[76] Inventor: John M. Levin, 412 Fairview Rd., Narbeth, Pa. 19072

[21] Appl. No.: 595,328

[22] Filed: Feb. 1, 1996

[51] Int. Cl.[6] ................................................... A61N 1/362
[52] U.S. Cl. ............................................................ 128/897
[58] Field of Search ..................................... 128/899, 897, 128/898; 600/16–18; 623/1–4

[56] References Cited

U.S. PATENT DOCUMENTS

| | | | |
|---|---|---|---|
| 3,910,283 | 10/1975 | Leveen . | |
| 4,240,433 | 12/1980 | Newkirk . | |
| 4,630,597 | 12/1986 | Kantrowitz et al. | 600/18 |
| 5,271,746 | 12/1993 | Pol et al. | 600/16 |
| 5,273,518 | 12/1993 | Lee et al. | 600/16 |
| 5,318,501 | 6/1994 | Lee et al. | 600/16 |

*Primary Examiner*—John P. Lacyk
*Assistant Examiner*—Samuel Gilbert
*Attorney, Agent, or Firm*—Caesar, Rivise, Bernstein, Cohen & Pokotilow, Ltd.

[57] ABSTRACT

An internal body pump is a continuous loop with a fluid therein. The continuous loop is extendable into areas of a person's body having different pressure levels. Preferably the loop extends through a person's diaphragm with a first portion of the loop being in the thoracic area above the diaphragm and a second portion of the loop being in the abdominal area below the diaphragm. The loop includes pressure responsive members or sections as a part thereof, preferably locatable in both the thoracic and abdominal areas, and fluid is caused to flow in the continuous loop due to changes in pressure conditions imposed upon the pressure responsive members or sections resulting from the breathing activity of the person.

A prosthesis for implanting in a patient's body has outer and inner walls defining a peripheral fluid channel therebetween for receiving the flow of a fluid therethrough. The inner wall provides the periphery of an internal chamber through said prosthesis. Preferably the inner wall is elastic and provides peristaltic action as fluid is directed through the fluid channel. The fluid channel is, a single compartment or includes multiple compartments separated by one-way valves. The prosthesis of this invention can be within the continuous loop of the internal body pump to direct fluid moving in the pump through the peripheral fluid channel of the prosthesis.

37 Claims, 5 Drawing Sheets

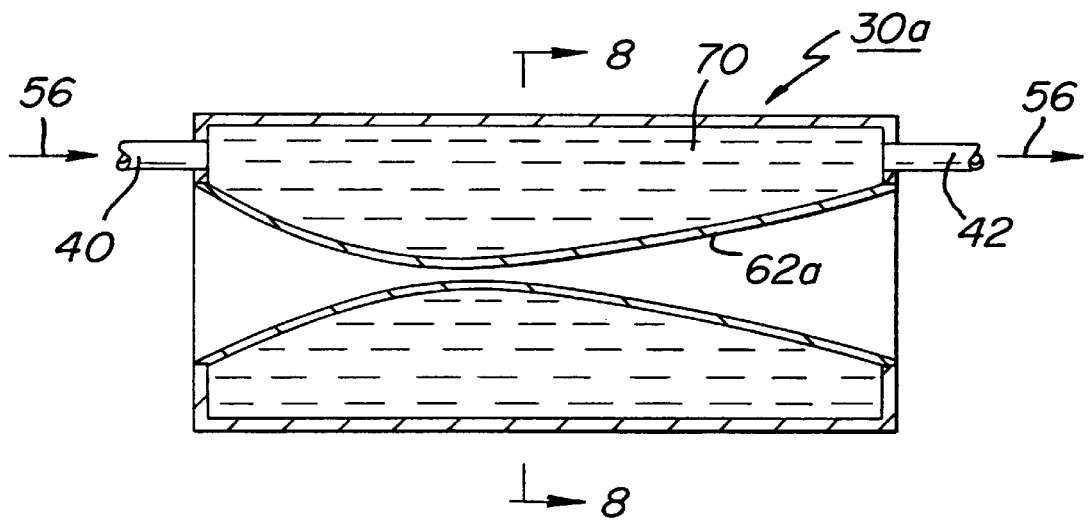
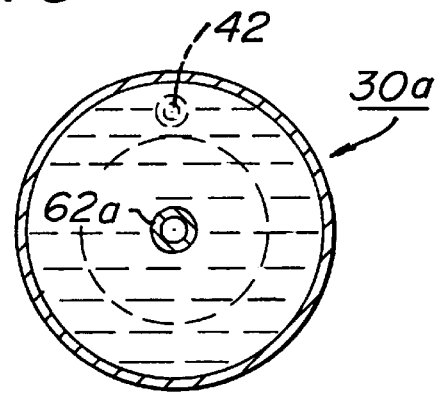
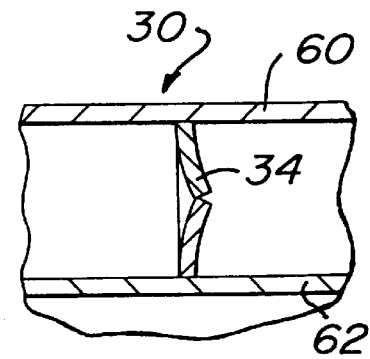
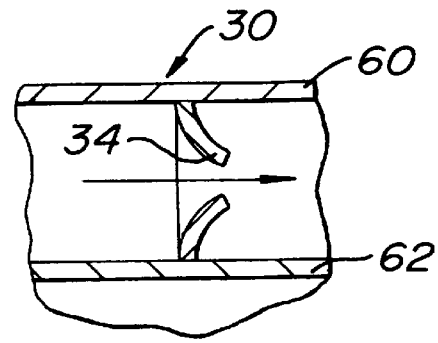

INTERNAL BODY PUMP AND SYSTEMS EMPLOYING SAME

SPECIFICATION

1. Field of the Invention

This invention relates generally to a unique internal body pump and to devices that are well suited for use with the pump, such as peristaltic prostheses and energy generating systems for pacemakers and other devices. Peristaltic prostheses included within this invention are usable as grafts for tubular and pouch-type body parts requiring peristaltic action (e.g., ureter and urinary bladder, respectively).

2. Background of the Invention

Internal shunts for treating ascites by moving the ascites from the peritoneal cavity into the vascular system are known (e.g., see U.S. Pat. Nos. 3,910,283 and 4,240,434). Although these shunts function by virtue of changes in cavity pressure depending on the phase of respiration, they are delivery devices having opposed ends located in the perineal cavity and vascular system, respectively. These shunts are significantly different in construction and mode of operation from the various devices forming the subject matter of this invention.

To applicant's knowledge there are has never been an internal body pump employing a continuous loop system and being capable of multiple physiological applications within the body, and that is operable on the basis of normal pressure variations that take place within the body as a result of a person's breathing pattern. It is to such a pump, and to unique systems employing the pump, that this invention relates.

As is well known, a variety of body parts/organs function, at least in part, through peristaltic action, e.g., major veins, esophagus, common bile duct, pancreatic duct, ureter, fallopian tube, urinary bladder, stomach, and the thoracic duct. When these parts become injured or diseased and require partial or complete removal and repair or replacement, it often is necessary to replace the injured or diseased section or body part with a prosthesis. However, until the present invention, known prostheses were not capable of providing peristaltic action, and therefore could not function for applications in which such action is required or desired for the proper functioning of the body part. In fact, such known prostheses are not utilized today for applications requiring peristaltic action. This invention relates to unique prosthesis capable of providing peristaltic action and useable both with and without the unique internal body pump of this invention.

Although mechanical hearts employing a pulsing action to move blood through them have been disclosed in the patent literature, e.g., U.S. Pat. No. 5,271,746, such pulsing action is not peristaltic action of the type required for grafts of the present invention. In fact, to characterize the pulsing action of mechanical hearts as peristaltic action is technically inaccurate. Moreover, these mechanical hearts are significantly different in structure and mode of operation from the devices of the instant invention.

SUMMARY OF THE INVENTION

One aspect of this invention is an internal body pump capable of multiple applications, and that functions to move a fluid in a continuous circulating loop, preferably a closed continuous circulating loop, by pressure variations that normally take place in a person's body do to the person's breathing pattern.

In accordance with this invention, an internal body pump implantable in a person includes conduit means for providing a passage for the fluid, said passage being in a continuous circulating loop capable of being located in sections of the body having different internal pressure levels, with the pressure level varying in at least one of said sections due to breathing activity of a person. Sections of the body in which the continuous circulating loop can pass include the interperitoneal and interplural cavities and extraperitoneal regions, e.g., retroperitoneal, mediastinal are or soft tissue.

The conduit means includes at least one pressure responsive section locatable in a section of the body in which the pressure level varies due to the breathing activity of the person in whom the pump is implanted, said pressure responsive section being capable of transmitting varying pressure from said section of the body to the fluid within the pressure responsive section for causing the fluid to move in the continuous circulating loop.

In accordance with this invention the pressure responsive section can be generally tubular or can be in the form of a collapsible sack having a larger fluid-retaining volume than connecting tubing of the conduit means.

Preferably, the pump includes a pair of pressure responsive sections; one being located in the thoracic area of the person and the other being located in the abdominal, or pertineal cavity of the person. Most preferably, the pressure responsive sections include a pair of sacks having a larger fluid-retaining volume than connecting tubing of the conduit means, with one of the sacks being in the thoracic area and the other of said sacks being in the peritoneal cavity.

In accordance with preferred features of this invention, fluid flow within the pump is created by taking advantage of the normal function of a person's diaphragm during breathing, and the normal internal pressure relationships that exist between the thoracic area and the abdominal area of the person's body. Specifically, during inspiration (inhaling) the diaphragm, which separates the thoracic and abdominal cavities, is forced to descend; thereby leading to an increase in the intrathoracic volume and a corresponding decrease in the intrathoracic pressure. Conversely the volume of the abdominal cavity decreases and the pressure in that cavity increases.

Upon expiration (exhaling) the operation of the diaphragm is reversed. That is, it is forced to rise; thereby leading to a decrease in the intrathoracic volume and a corresponding increase in the intrathoracic pressure. Conversely, during expiration the volume of the abdominal cavity increases and the pressure in that cavity decreases. Under both conditions of inspiration and expiration the absolute pressure in the abdominal cavity is greater than the absolute pressure in the thoracic area. These pressure relationships created in part by the person's breathing pattern are taken advantage of in the preferred embodiments of the internal pump of this invention, wherein pressure responsive sections are located in both the thoracic and abdominal areas of the person.

It is within the broadest aspects of this invention to include either a miniature mechanical or electrical pump or motor in conjunction with the internal body pump, either located completely within the person's body or located partially outside of the patient's body, to provide a pressure assist to move fluid within the continuous loop, if needed.

This invention also relates to a prosthesis, or graft, capable of peristaltic action, and which is well-suited for use with the internal body pump of this invention, although it can be used with other pumping systems. In fact, the prosthetic grafts of this invention are believed to be the first known prosthetic grafts providing peristaltic action.

In accordance with this invention, the prosthetic grafts are designed with one or more fluid-receiving compartments therein, and fluid is directed through these compartment(s) in a manner to generate peristaltic action.

Reference to "peristaltic" as used throughout this application to describe the action or mode of operation of the prosthesis refers to a repeating, continuous and progressive wave-like motion of a wall of the prosthesis along a predetermined direction of the prosthesis.

This invention also relates to the inclusion of an electrical energy generating source, such as a micro-turbine, in the closed loop system of the internal body pump for generating electrical energy. In accordance with this aspect of the invention, a wheel, blades, or other moveable member of the micro-turbine preferably is located within the closed loop system to be driven by fluid flowing therein to generate electrical energy. This electrical energy can be employed to assist in driving a number of different devices, e.g., a pacemaker, an ACID, i.e., an insertable defribulating device, or even a mechanical heart.

BRIEF DESCRIPTION OF THE DRAWINGS

Other objects and many of the intended advantages of this invention will be readily appreciated when the same becomes better understood by reference to the following detailed description, when considered in connection with the accompanying drawing wherein:

FIG. 7 is a sectional view similar to FIG. 3, but showing an alternative form of peristaltic graft in accordance with this invention;

FIG. 8 is a sectional view taken along line 8—8 of FIG. 7;

FIG. 9 is an enlarged view of the circled region of FIG. 3, but with the valve closed;

FIG. 10 is an enlarged view of the circled region of FIG. 3, but with the valve opened, as illustrated in FIG. 3;

DESCRIPTION OF THE PREFERRED EMBODIMENTS OF THE INVENTION

Figure 1:
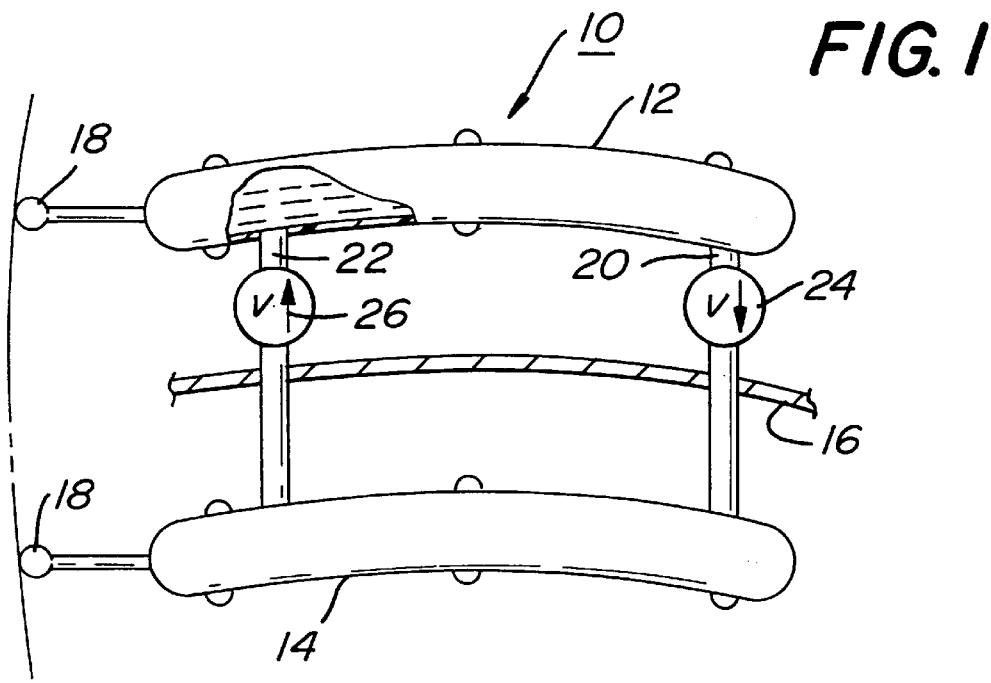
FIG. 1 is an elevational view of a unique internal body pump of this invention, showing its preferred location relative to the diaphragm within the body.

Referring now in greater detail to the various figures of the drawing, wherein like reference characters refer to like parts, there is shown in FIG. 1 an unique internal body pump 10 in accordance with one preferred aspect of the instant invention. In the preferred embodiment of this invention, a pair of fluid-retaining sacks 12 and 14 are disposed on opposite sides of a person's diaphragm 16 and can be secured to the opposed walls of the diaphragm by sutures or other suitable means (not shown), i.e., one in the thoracic area and the other in the abdominal area. For purposes of clarity, to illustrate the various parts of the pump 10, the sacks 12 and 14 are shown spaced-apart from the diaphragm 16 in FIG. 1.

Most preferably, the upper sack 12 should be located in the costo-phrenic sulcus (i.e., the lateral angle of the plural space where, during expiration, the sack will be squeezed between the lung above it, the liver below it (which acts through the diaphragm) and the body, or chest wall.

In the preferred form of the invention, the sacks 12 and 14 are formed of an inelastic but flexible plastic material compatible with the body, and initially are completely flat, with all of the air having been removed from them, i.e., they have been evacuated and therefore are under vacuum conditions. In use these sacks are only partially filled with a saline solution or with another solution that is compatible with the body.

In an exemplary embodiment of the invention, and not by way of limitation, each of the sacks 12 and 14 has an internal compartment adapted to receive up to 200 cc of solution, and in use each compartment is filled about half-full, with approximately 100 cc of solution.

Still referring to FIG. 1, to assist in filling each of the sacks 12 and 14, a subcutaneous access reservoir 18 is provided in communication with each sack and positioned closely adjacent the person's skin so that each sack can be filled percutaneously with a small syringe, with the plastic material of the reservoir 18 having the ability to reseal itself after the need of the syringe has been removed. Alternatively, the subcutaneous access reservoir 18 could be omitted, in which case the sacks could be filled by directly piercing the walls of the sack, or alternatively each of the sacks could be fitted with a conventional fill-valve (not shown) through which the filling operation could be achieved. If the filling operation is to take place by directly piercing the wall of each sack 12 and 14, then the plastic material forming the sack should also have the capability of resealing itself after the needle of the filling syringe is removed.

Still referring to FIG. 1, the sacks 12 and 14 are interconnected to each other by connecting conduits 20 and 22 that pass through the diaphragm 16 to provide a closed loop system. A one-way valve 24, 26 is provided in each of the conduits 20, 22, respectively, to direct fluid-flow through each of the conduits in only one direction. As illustrated in FIG. 1, the valves 24 and 26 control the flow of fluid through the pump 10 in a clockwise direction. If required, additional one-way valves can be included in the system at other locations.

As explained earlier in this application, fluid flow by the pump 10 is created by taking advantage of the normal function of a person's diaphragm, and the normal internal pressure relationships that exist between the thoracic area and the abdominal area of the person's body. Specifically, and as explained earlier, during inspiration (inhaling) the diaphragm, which separates the thoracic and abdominal cavities, is forced to descend; thereby leading to an increase in the intrathoracic volume and a corresponding decrease in the intrathoracic pressure. Conversely the volume of the abdominal cavity decreases and the pressure in that cavity increases. This action forces fluid from the sack 14 located in the abdominal cavity through conduit 20 and into the sack 12 in the thoracic area. It should be noted that flow from the sack 14 to the sack 12 is limited to flowing through the conduit 20 do to the arrangement of the one-way valves 24, 26 in the respective conduits 20 and 22.

Upon expiration (exhaling) the operation of the diaphragm is reversed. That is, it is forced to rise; thereby leading to a decrease in the intrathoracic volume and a corresponding increase in the intrathoracic pressure. Conversely, during expiration the volume of the abdominal cavity increases and the pressure in that cavity decreases. This action forces fluid from the sack 12 located in the thoracic area, and preferably in the costo-phrenic sulcus thereof, through conduit 22 and into the sack 14 located in the abdominal cavity. It should be noted that flow from the sack 12 to the sack 14 is limited to flowing through the conduit 22 do to the arrangement of the one-way valves 24, 26 in the respective conduits 20 and 22.

Although in the preferred embodiments of the pump 10 fluid-containing sacks 12 and 14 are included on both sides of the diaphragm, it is within the scope of this invention to employ a fluid-containing sack on only one side of the diaphragm, and rely solely upon pressure variations in the area of the body in which that sack is retained to provide the motive power to maintain fluid-flow in the closed loop system through the pump. This is not the most preferred form of the invention because fluid flow through the system will be slower than can be achieved with the use of fluid-containing sacks disposed on both sides of the diaphragm, and therefore the pulsatile flow of fluid through the pump may not be adequate for certain applications, such as when the flow is required to impart peristaltic action to a graft. Specifically, the peristaltic action created in a graft by a pump employing only one sack will not be as pronounced as in a graft connected in series with sacks located on opposite sides of a person's diaphragm. However, for some applications, the degree of peristaltic action achieved through the use of a sack located only on one side of the diaphragm may be adequate.

It also is within the scope of this invention to utilize flexible tubing in place of one or both of the sacks 12 and 14 of the pump, provided that such flexible tubing responds to the pressure variations/conditions in the thoracic area and/or abdominal area in the same manner as the sacks 12 and 14, to create the motive power for moving the fluid through the pump.

The prosthesis, or grafts, in accordance with this invention include a peripheral, fluid-retaining chamber consisting of one or more closed compartments, and these prosthesis preferably are connected in series with the sacks 12 and 14 of the pump 10 through connecting conduits to form a closed-loop system.

Referring specifically to FIGS. 2–6, the use of the internal body pump 10 described above is shown in combination with a unique prosthesis, or graft, 30, that functions with peristaltic action.

Figure 2:
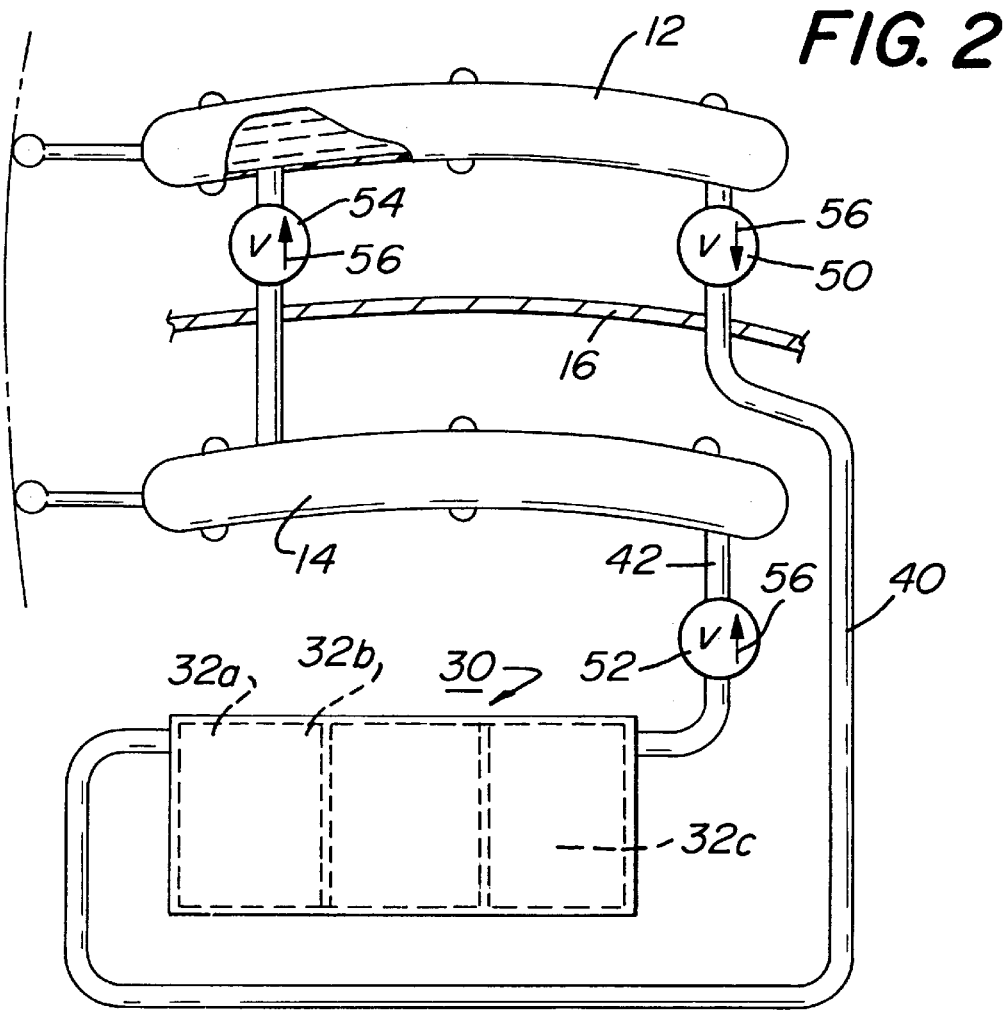
FIG. 2 is an elevational view of the unique internal body pump shown in FIG. 1, but employed in conjunction with a peristaltic graft in accordance with this invention.
Figure 3:
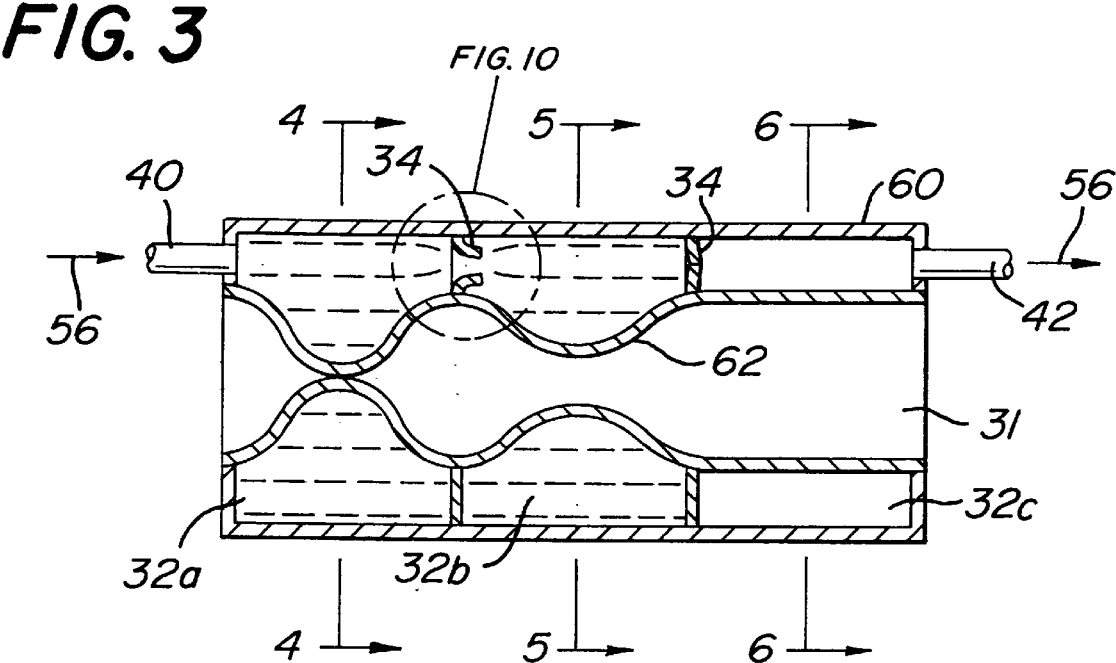
FIG. 3 is a sectional view through the graft illustrated in FIG. 2, and schematically illustrating the peristaltic action.
Figure 4:
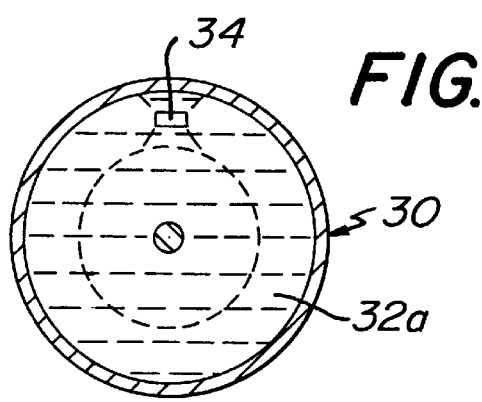
FIG. 4 is a sectional view taken along line 4—4 of FIG. 3.
Figure 5:
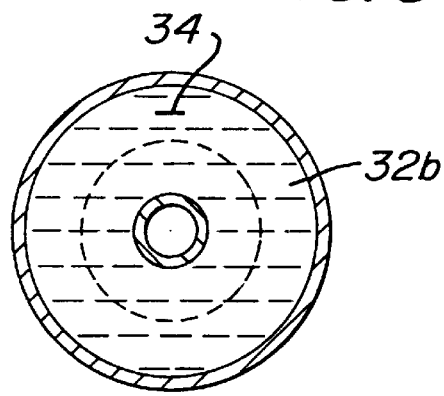
FIG. 5 is a sectional view taken along line 5—5 of FIG. 3.
Figure 6:
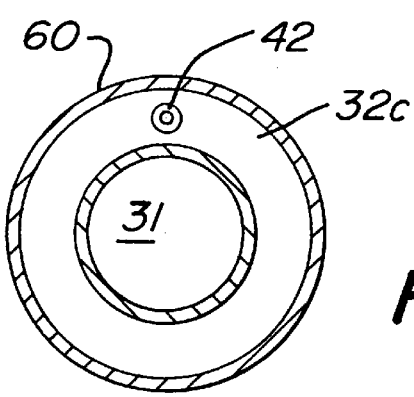
FIG. 6 is a sectional view taken along line 6—6 of FIG. 3.

In the embodiment illustrated in FIGS. 2–6, the prosthesis 30 is in the form of an annular member suitable for use in the repair of a vein, and, as can be seen best in FIG. 3, this member includes a peripheral, fluid-retaining chamber in the form of three compartments 32a, 32b and 32c disposed in series and interconnected to each other through a series of one way valves 34. Enlarged views of a one-way valve 34 in a closed and opened condition are shown in FIGS. 9 and 10, respectively. The arrangement of valves 34 permits fluid flow through the compartments 32a, 32b and 32c only in the direction of arrows 56. It should be understood that the number of compartments employed in the prosthesis can be varied, and can even by a single compartment, as will be described in detail later in this application.

The sack 12 located in the thoracic area of the body is interconnected to an end chamber 32a at the proximal end of the prosthesis 30 through a conduit 40. A second conduit 42 communicates an end chamber 32c at the opposite, or distal, end of the prosthesis 30 with the sack 14 located in the abdominal area of the body, and the two sacks 12 and 14 are interconnected to each other through the diaphragm by a third conduit 44. The conduits 40, 42 and 44 include one-way valves 50, 52, and 54, respectively, therein to control the flow of saline, or other solution through the closed loop system only in the direction of arrows 56. This direction of flow is achieved by the inclusion of the one-way valves in the system and, in part, because the pressure in the abdominal cavity, to which the sack 14 is exposed, is always higher than the pressure in the thoracic cavity, to which the sack 12 is exposed. The one-way valve system insures that no undesired reverse flow occurs, such as might be the case if conditions within the body are upset, e.g., by a person sneezing, coughing, etc. Also, if required, additional one-way valves can be included in the system to assist in controlling the direction of fluid flow therein.

The variation in pressure conditions between the thoracic area and the abdominal area causes a pulsatile flow of the solution through the conduits 40, 42 and 44, and through the graft 30. As will be explained in detail hereinafter, this pulsatile flow of the saline, or other solution, causes a peristaltic action in the graft 30.

In the preferred embodiment of this invention the prosthesis 30 includes an outer wall 60 formed of a non-expansible material, such as a reinforced dacron mesh fabric, and an inner wall 62 formed of an expansible or elastic material. When the elastic inner wall associated with each of the compartments 32a, 32b and 32c is exposed to the pulsatile flow of the saline solution moving through them, the inner wall associated with each of said compartments will alternately expand and retract to provide the peristaltic action. This peristaltic action, at a specific instance in time, is schematically illustrated in FIG. 3. For some applications it may not be necessary to form the outer wall 60 of the prosthesis of a non-expansible material, and therefore, in accordance with the broadest aspects of this invention the outer wall is not required to be non-expansible.

In accordance with the most preferred forms of the invention, the continuous, pulsatile flow that creates the peristaltic action is achieved by taking advantage of normal pressure effects/conditions within the body. In particular, in the preferred form of the invention described above, this pulsatile flow is achieved by taking advantage of the fact that the pressure in the abdominal cavity is greater than that in the thoracic area, and that the pressure conditions within both the abdominal cavity and thoracic area vary in a rhythmic manner during normal breathing, as described above. The peristaltic action of the graft 30 effectively acts upon fluid (e.g. blood) flowing through central passage 31 of said graft.

Referring to FIGS. 7 and 8, an alternative embodiment of a prosthesis is shown at 30a. This prosthesis, like the prosthesis 30, is annular in configuration. However, the prosthesis 30a differs from the prosthesis 30 in that it includes an internal peripheral chamber in the form of a single compartment 70, rather than multiple compartments 32a, 32b and 32c. The conduits 40 and 42 are connected to opposite ends of the prosthesis 30a in the same manner as described above in connection with the prosthesis 30. For certain applications the pulsatile flow created in the system will induce a sinusoidal-type peristaltic action on inner wall 62a of the prosthesis 30a, as is schematically illustrated in FIG. 7, even though the internal chamber is not divided into multiple compartments as in the prosthesis 30.

Figure 11:
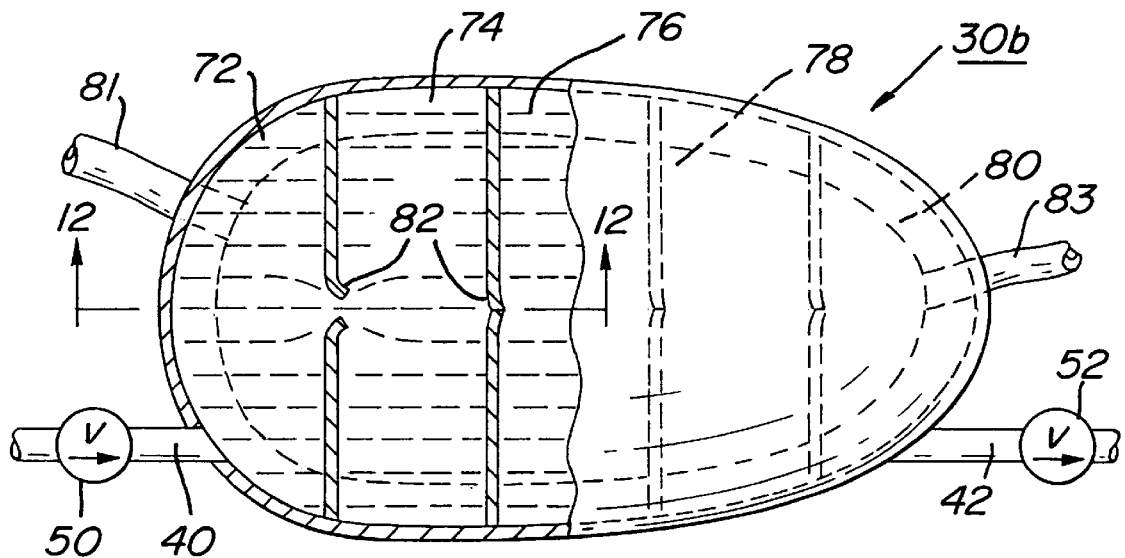
FIG. 11 is an elevational view of a prosthetic graft for replacing a urinary bladder, with parts broken away to show internal details of construction.
Figure 12:
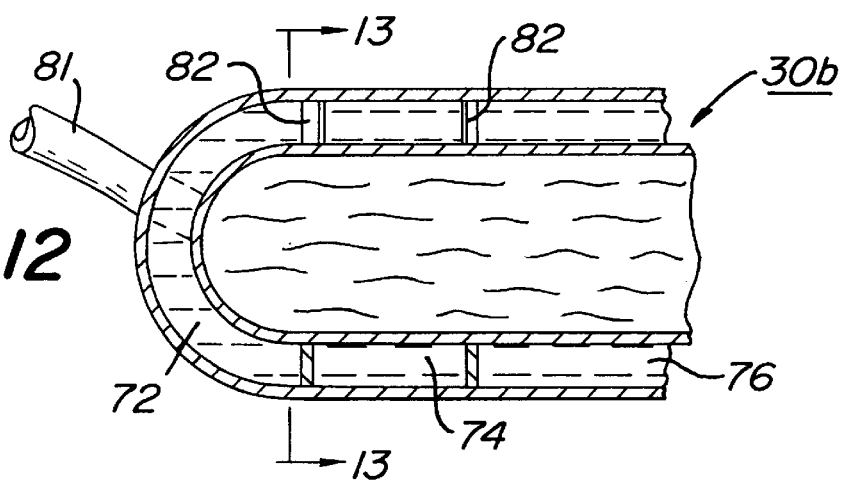
FIG. 12 is a sectional view taken along line 12—12 of FIG. 11.
Figure 13:
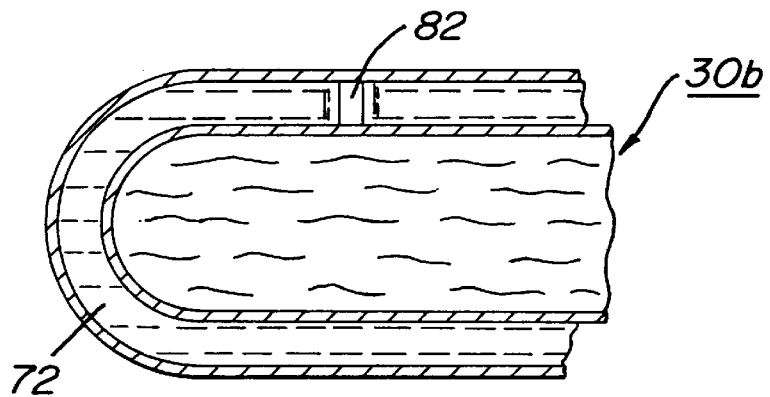
FIG. 13 is a sectional view taken along line 13—13 of FIG. 12.

Referring to FIGS. 11–13, another alternative embodiment of a prosthesis is shown at 30b. This prosthesis is of a laminate construction, and, as illustrated, is shaped to replace an injured urinary bladder. In the illustrated embodiment, an inlet 81 and an outlet 83 are provided to and from the internal cavity of the prosthesis 30b. In addition, the prosthesis includes an internal peripheral chamber formed of multiple compartments 72, 74, 76, 78 and 80 interconnected by one-way valves 82 in the same manner as disclosed in connection with the prosthesis 30. Moreover, the conduits 40 and 42 of the pump, with the one-way valves therein, are interconnected to compartments 72 and 80 of the internal peripheral chamber of the prosthesis 30b. It should be understood that the prosthesis 30b is connected to the pump in the same manner that the prosthesis 30 illustrated in FIG. 2 is connected to the pump.

For some applications, the internal peripheral chamber of the prosthesis 30b may be formed as a single, uninterrupted compartment, similar to that employed in the prosthesis 30a illustrated in FIG. 7. However, such a single, uninterrupted compartment still will conform generally to the shape or configuration of the prosthesis 30b.

It is also within the scope of this invention to vary the configuration of the internal peripheral chamber, whether said chamber is formed of a single, or multiple compartments. For example the internal chamber can be formed in a spiral array through the prosthesis, and be either a single, or multiple compartment chamber. Other chamber configurations may also be usable within the scope of this invention.

It should be understood that the specific pressure conditions established in the system will control, to a significant degree, the nature of the continuous, pulsatile flow responsible for creating the peristaltic action in the various grafts of this invention, and that this pressure will be determined by the specific application or use of the prosthesis. For example, the pressure conditions required for establishing the desired peristaltic action in a graft or prosthesis for the ureter will most likely be different form the pressure conditions required for establishing the desired peristaltic action in a graft or prosthesis for the esophagus, or for a vein. Pressure conditions in accordance with this invention can be varied in a number of ways, e.g., changing the diameter of the conduits 40, 42 and 44; varying the size, or fluid-holding capacity of the sacks 12, 14; varying the volume of solution to be moved through the system, varying the pressure-responsive behavior of the one-way valves utilized in the system, varying the materials utilized in the prosthesis and varying the volume of the chamber/compartment(s) within the prosthesis.

It should be understood that the specific one-way valves disclosed herein are not considered to be a limitation on the present invention, since a variety of different one-way valves are considered usable in this invention. The most common types of valves being utilizable in this invention are miter valves or a ball valves.

Although in the preferred embodiments of this invention normal pressure conditions, including variations in such pressure conditions, are taken advantage of to create the pulsatile flow for establishing the peristaltic action of the various prosthesis of this invention, it is within the scope of this invention to utilize an external source, such as an electric motor adaptable for use in the body, to move the fluid through the prosthesis in a rhythmic, or pulsatile flow. Thus, in accordance with the broadest aspects of this invention, the internal body pump disclosed in detail herein need not be used with the peristaltic prosthesis of this invention.

It also should be understood that the shape/configuration of the prosthesis can be varied in accordance with this invention, and indeed needs to be varied to accommodate the specific area of use. In fact, in applications wherein the prosthesis is intended to replace an entire organ, e.g., the urinary bladder, the prosthesis desirably will be configured to the approximate shape of that organ.

Figure 14:
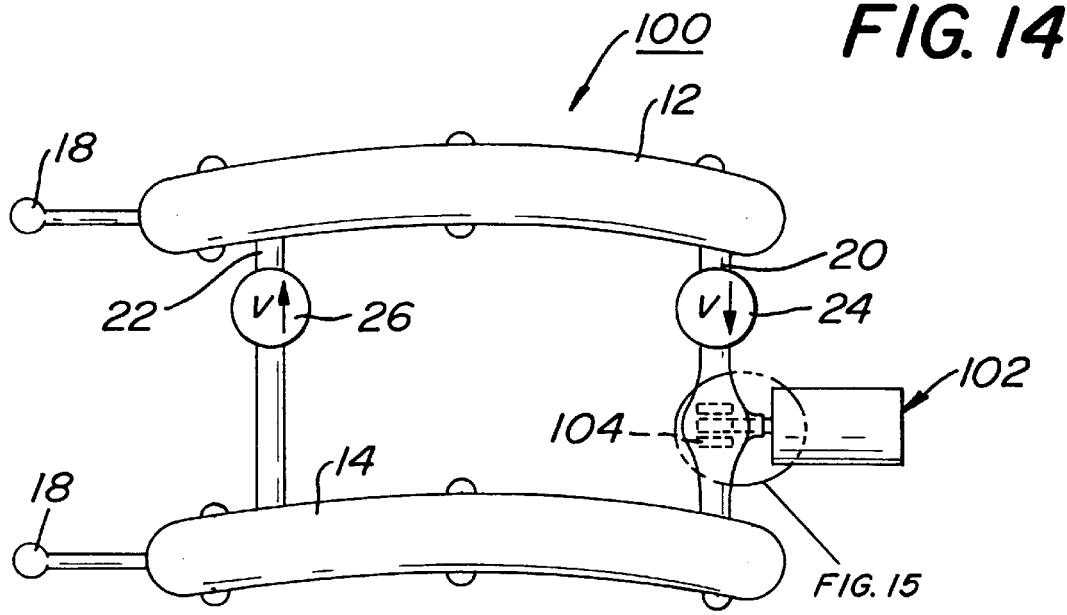
FIG. 14 is an elevational view of the unique internal body pump shown in FIG. 1, but employed in conjunction with a system for generating electrical energy in accordance with this invention.
Figures 15, 16:
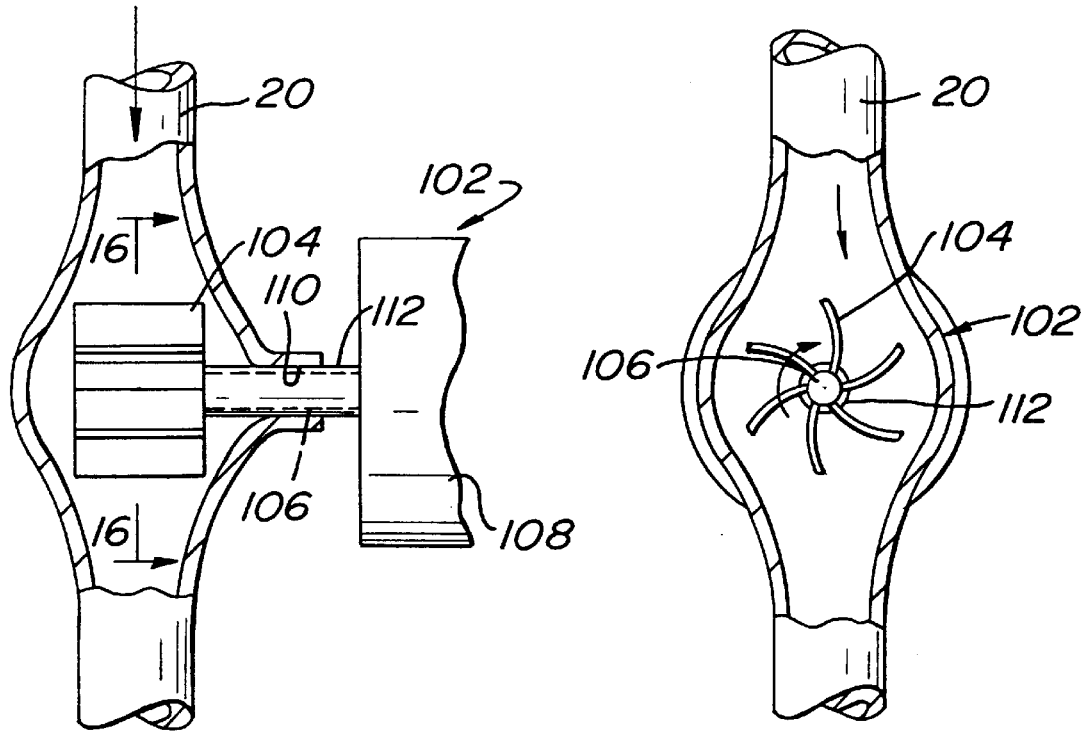
FIG. 15 is an enlarged sectional view of the circled region of the pump including the micro-turbine arrangement for generating electrical energy in the device illustrated in FIG. 14.
FIG. 16 is an enlarged sectional view taken along line 16—16 of FIG. 15.

Referring to FIGS. 14 through 16, still another system of the invention utilizing the internal body pump discussed earlier is generally shown at 100. The system 100 includes the same arrangement of sacks 12 and 14, subcutaneous access reservoirs 18, conduits 20 and 22, and one-way valves 24 and 26 as employed in the pump 10 illustrated in FIG. 1. However, in the system 100 a micro-turbine 102 is mounted or secured to the conduit 20, with the blades or wheel 104 thereof being disposed inside the conduit 20 and being connected through a rotary shaft 106 to the energy-generating section 108 of the turbine. In this embodiment the continuous flow of fluid through the conduit 20 rotates the turbine blades 104 to generate electrical energy for any desired function, e.g., controlling the operation of a pacemaker, an ACID, or even a mechanical heart. As is illustrated, the conduit 20 includes a flanged opening 110, the walls of which are secured through a fluid-tight seal by any suitable bonding agent to an outer cylindrical housing 112 through which the rotary shaft 106 connected to the wheel 104 extends. It should be understood that a pump employing only a single sack located either in the thoracic area or abdominal area, or a pump employing deformable tubular members in one or both of said thoracic and abdominal areas may be usable in this form of the invention for generating electrical energy.

What I claim is:

1. An internal body pump implantable in a person's body for circulating a fluid in a continuous loop within the person's body, said pump including conduit means for providing a passage for the fluid, said passage being in a continuous circulating loop including portions capable of being located in areas of the body having different internal pressure levels, with the pressure level varying in at least one of said areas of the body due to breathing activity of a person, said conduit means including at least one pressure responsive section locatable in an area of the body in which a varying pressure level occurs due to the breathing activity of the person in whom the pump is implantable, said pressure responsive section being responsive to said varying pressure level so as to be capable of transmitting varying pressure from said area of the body to the fluid within the pressure responsive section for causing the fluid to move in a continuous circulating loop of the pump.

2. The internal body pump of claim 1, including a pair of pressure responsive sections, said sections being in portions of the loop adapted to be located in different areas of the body.

3. The internal body pump of claim 2, wherein said pair of pressure responsive sections are each a deformable tubular conduit section.

4. The internal body pump of claim 3, wherein said continuous loop is a closed loop.

5. The internal body pump of claim 2, wherein said pair of pressure responsive sections are deformable sacks having a fluid-retaining volume greater than tubular sections of the conduit means connected to said sacks.

6. The internal body pump of claim 5, wherein said continuous loop is a closed loop.

7. The internal body pump of claim 2, wherein said continuous loop is a closed loop.

8. The internal body pump of claim 1, including a pair of pressure responsive sections, one of said pressure responsive sections being in a first portion of the loop adapted to be located in a first area of the body and the other of said pressure responsive sections being located in a second portion of the loop adapted to be located in said second area of the body, the internal pressure in said first and second areas of the body varying during the breathing activity of the person with the pressure in said first area always being different than the pressure in slid second area.

9. The internal body pump of claim 8, wherein said pair of pressure responsive sections are deformable sacks having a fluid-retaining volume greater than tubular sections of the conduit means connected to said sacks.

10. The internal body pump of claim 9, wherein said continuous loop is a closed loop.

11. The internal body pump of claim 8, wherein said pair of pressure responsive sections are each a deformable tubular conduit section.

12. The internal body pump of claim 4, wherein said continuous loop is a closed loop.

13. The internal body pump of claim 8, wherein said continuous loop is a closed loop.

14. The internal body pump of claim 3, including one-way valve means in said continuous loop for causing the fluid to flow in only one direction within said loop.

15. The internal body pump of claim 1, wherein said at least one pressure responsive section is a deformable tubular conduit section.

16. The internal body pump of claim 15, wherein said continuous loop is a closed loop.

17. The internal body pump of claim 1, wherein said at least one pressure responsive section is a deformable sack having a fluid-retaining volume greater than tubular sections of the conduit means connected to said sacks.

18. The internal body pump of claim 17, wherein said continuous loop is a closed loop.

19. The internal body pump of claim 1, including one-way valve means in said continuous loop for causing the fluid to flow in only one direction within said loop.

20. The internal body pump of claim 1, wherein said continuous loop is a closed loop.

21. The internal body pump of claim 1, wherein said areas of the body include first and second areas located on opposite sides of the person's diaphragm and the continuous loop being extendable through the diaphragm with a first portion of said loop being locatable in the thoracic area above the diaphragm and a second portion of said loop being locatable in the abdominal area below the diaphragm, said at least one pressure responsive section being locatable in one of said thoracic areas or abdominal areas.

22. The internal body pump of claim 21, including one-way valve means in said continuous loop for causing the fluid to flow in only one direction.

23. The internal body pump of claim 21, wherein said at least one pressure responsive section is a fluid-retaining sack, said continuous loop including a pair of flexible conduits communicating with said sack for directing said fluid into and out of said sack as said fluid flows in said continuous loop.

24. The internal body pump of claim 23, including one-way valve means in said continuous loop for causing the fluid to flow in only one direction.

25. The internal body pump of claim 23, including a reservoir connected to said at least one fluid-retaining sack of said continuous loop and adapted to be disposed internally of the person's body adjacent the person's skin to permit percutaneous access to said at least one of said fluid-retaining sacks of said continuous loop through said reservoir.

26. The internal body pump of claim 21, wherein said continuous loop includes a pair of pressure responsive sections in the form of fluid-retaining sacks, one of said fluid-retaining sacks being locatable in said thoracic area and the other of said fluid-retaining sacks being locatable in said abdominal area, and conduit means being extendable through the person's diaphragm for communicating each of said sacks with the other of said sacks in two locations for permitting fluid to flow from one of said locations in one fluid-retaining sack to one of said locations in the other fluid-retaining sack and from the other of said locations in the other fluid-retaining sack to the other of said locations in said one fluid-retaining sack.

27. The internal body pump of claim 26, including one-way valve means in said continuous loop for causing the fluid to flow in only one direction in said system.

28. The internal body pump of claim 27, wherein said one-way valve means are included in said conduit means.

29. The internal body pump of claim 25, including a reservoir connected to each of said fluid-retaining sacks of said continuous loop, each of said reservoirs adapted to be disposed internally of the person's body adjacent the person's skin to permit percutaneous access to each of said fluid-retaining sacks of said continuous loop.

30. The internal body pump of claim 21, including a reservoir connected to the continuous loop and adapted to be disposed internally of the person's body adjacent the person's skin to permit percutaneous access to the continuous loop through said reservoir.

31. The internal body pump of claim 21, wherein said continuous loop further includes a prosthesis therein, said prosthesis including outer and inner walls defining a fluid channel therebetween for receiving the flow of said fluid therethrough, said inner wall providing the periphery of an internal chamber in said prosthesis.

32. The internal body pump of claim 31 wherein said fluid channel of said prosthesis includes multiple compartments in series with each other, said channels being separated from each other by valve means for permitting fluid to flow in only one direction through said compartments.

33. The internal body pump of claim 32, wherein the inner wall of the prosthesis in each compartment is elastic and deforms as fluid is moved through the prosthesis to provide a peristaltic action.

34. The internal body pump of claim 33, wherein said internal chamber is in the form of a through passage extending from a proximal end of said prosthesis to a distal end of said prosthesis.

35. The internal body pump of claim 31, wherein said internal chamber is in the form of a through passage extending from a proximal end of said prosthesis to a distal end of said prosthesis.

36. The internal body pump of claim 31, wherein the inner wall of the prosthesis is elastic and deforms as fluid is moved through the prosthesis to provide a peristaltic action.

37. The internal body pump of claim 34, wherein said internal chamber is in the form of a through passage extending from a proximal end of said prosthesis to a distal end of said prosthesis.

* * * * *